US00PP22217P2

(12) United States Plant Patent
Uebelhart

(10) Patent No.: US PP22,217 P2
(45) Date of Patent: Oct. 25, 2011

(54) ***GAILLARDIA* PLANT NAMED 'JAZZY WHEELER'**

(50) Latin Name: *Gaillardia aristata*
Varietal Denomination: Jazzy Wheeler

(75) Inventor: Georg G. Uebelhart, Schwarmstedt (DE)

(73) Assignee: Jelitto Staudensamen GmbH, Schwarmstedt (DE)

( * ) Notice: Subject to any disclaimer, the term of this patent is extended or adjusted under 35 U.S.C. 154(b) by 0 days.

(21) Appl. No.: 12/803,790

(22) Filed: Jul. 7, 2010

(51) Int. Cl.
*A01H 5/00* (2006.01)

(52) U.S. Cl. ..... Plt./431

(58) Field of Classification Search ..... Plt./431
See application file for complete search history.

*Primary Examiner* — Annette Para
(74) *Attorney, Agent, or Firm* — Penny J. Aguirre

(57) ABSTRACT

A new cultivar of *Gaillardia*, 'Jazzy Wheeler', characterized by its large inflorescences with ray florets that exhibit yellow-orange centers and yellow tips, its numerous blooms produced throughout the growing season, and its dwarf, spreading habit and reliably perennial plant habit with hardiness in U.S.D.A. Zones 3 to 9.

2 Drawing Sheets

Botanical classification: *Gaillardia aristata.*
Variety denomination: 'Jazzy Wheeler'.

CROSS REFERENCE TO A RELATED APPLICATION

This application is co-pending with a U.S. Plant Patent Application filed for a plant derived the Inventor's breeding program that is entitled *Gaillardia* Plant Named 'Fancy Wheeler' (U.S. Plant Pat. No. 22,016).

BACKGROUND OF THE INVENTION

The present invention relates to a new and distinct cultivar of *Gaillardia* plant, botanically known as *Gaillardia aristata* 'Jazzy Wheeler' and will be referred to hereinafter by its cultivar name, 'Jazzy Wheeler'.

'Jazzy Wheeler' was derived from a controlled breeding program conducted by the Inventor at a nursery in Schwamstedt, Germany. The breeding program focuses on obtaining new cultivars of *Gaillardia* with compact and floriferous plant habit in a range of flower colors. 'Jazzy Wheeler' was selected in 2006 by the Inventor as a single unique plant derived from a cross made in 2005 between unnamed plants from his breeding program with the female parent identified with accession No. G04051 and the male parent identified with accession No. G04045.

Asexual reproduction of the new cultivar was first accomplished via stem cuttings in Lisse, The Netherlands in 2006. The characteristics of this cultivar have been determined to be stable and are reproduced true to type in successive generations.

SUMMARY OF THE INVENTION

The following traits have been repeatedly observed and are determined to be the characteristics of the new cultivar of *Gaillardia*. These attributes in combination distinguish 'Jazzy Wheeler' as unique from all other varieties of *Gaillardia* known to the inventor.

1. 'Jazzy Wheeler' exhibits large inflorescences with ray florets that exhibit yellow-orange centers and yellow tips.
2. 'Jazzy Wheeler' is hardy in U.S.D.A. Zones 3 to 9.
3. 'Jazzy Wheeler' is reliably perennial with a dwarf, spreading habit.
4. 'Jazzy Wheeler' produces numerous blooms throughout the growing season.

'Jazzy Wheeler' can be compared to its parents. The female parent differs from 'Fancy Wheeler' in having red coloration on the ray florets and being less vigorous. The male parent differs from 'Fancy Wheeler' in having red coloration on the ray florets. 'Fancy Wheeler' can also be compared to *Gaillardia* cultivars 'Arizona Sun', 'Primavera' (both unpatented) and 'Oranges and Lemons' (U.S. Plant Pat. No. 17,092). 'Arizona Sun' and 'Primavera' differ in having taller habits, smaller blooms and shorter blooming periods, and inflorescences that are less uniformly bi-colored. 'Arizona Sun' and 'Primavera' also differ in being less reliably perennial. 'Oranges and Lemons' differs in having a taller habit, smaller inflorescences, and in being less reliably perennial. 'Jazzy Wheeler' can also be compared to 'Fancy Wheeler' that differs from 'Jazzy Wheeler' in having inflorescences with ray florets that exhibit red centers with yellow tips.

BRIEF DESCRIPTION OF THE DRAWINGS

The accompanying colored photographs illustrate the overall appearance and distinct characteristics of the new *Gaillardia*. The photographs were taken of a plant two years in age as grown outdoors in a 1-gallon container in Lisse, the Netherlands.

The photograph in FIG. 1 is a side view of 'Jazzy Wheeler' in bloom.

Figure 1:
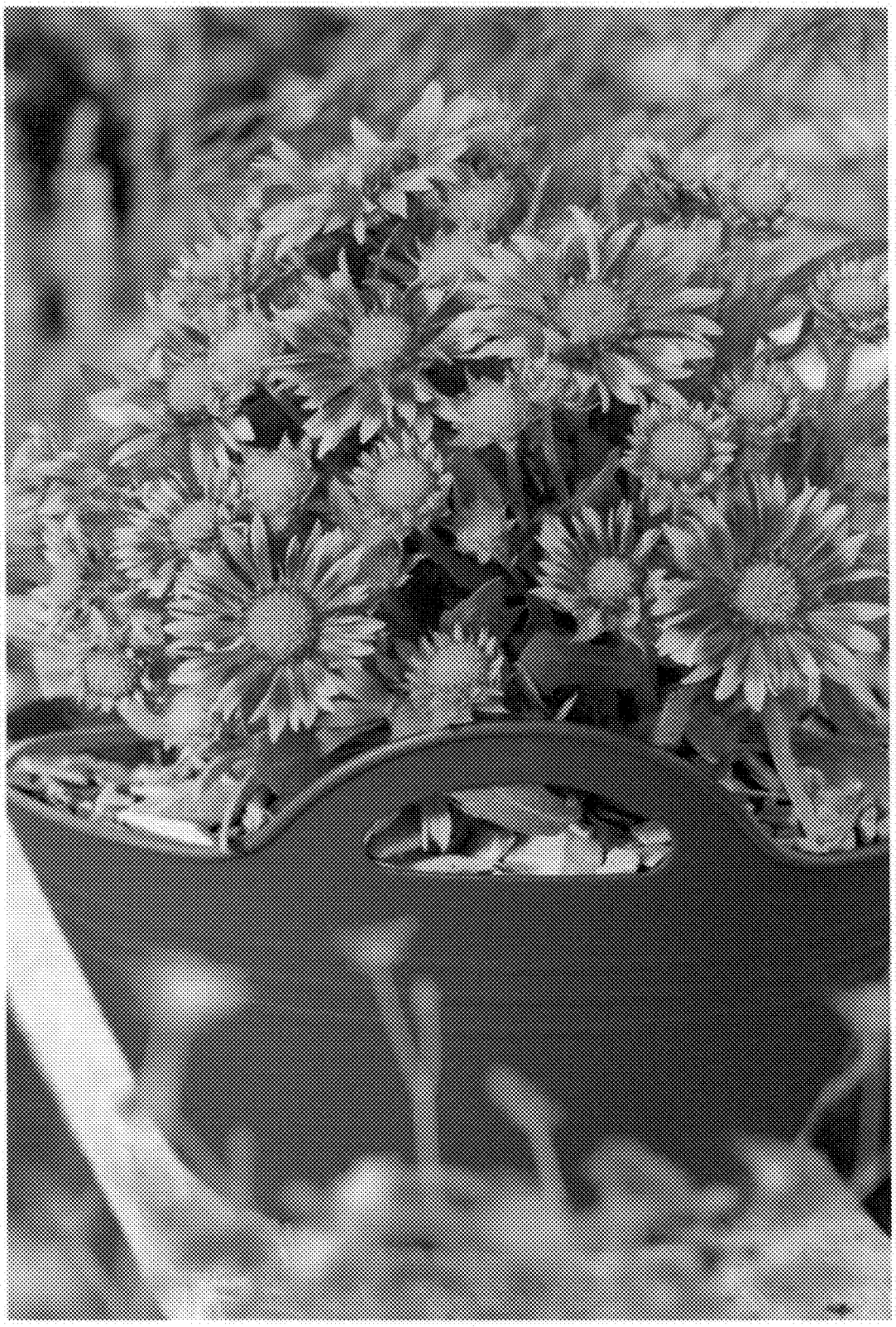
Figure 2:
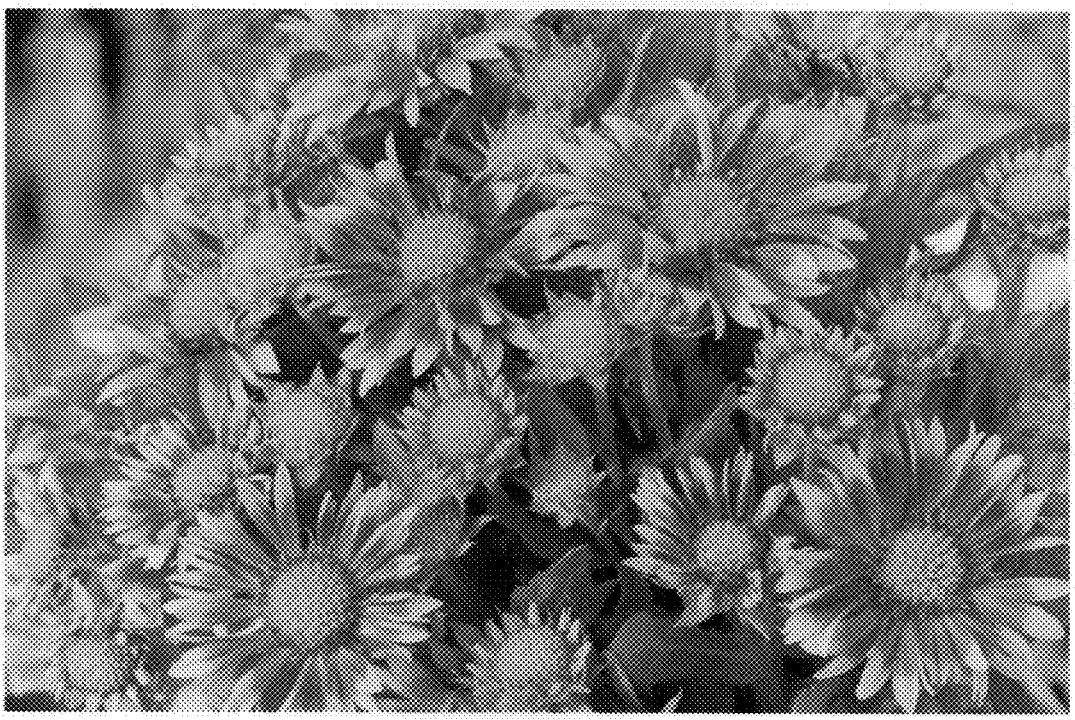

The photograph in FIG. 2 provides a close-up view of an inflorescence of 'Jazzy Wheeler'. The colors in the photographs are as close as possible with the digital photography and printing techniques utilized and the color codes in the detailed botanical description more accurately describe the colors of the new *Gaillardia.*

DETAILED BOTANICAL DESCRIPTION

The following is a detailed description of the new cultivar as grown outdoors under natural lighting in a trial bed in Waseca, Minn. and observed over a period of two years. The detailed botanical data was collected from three year-old plants grown in 4-liter containers in a cold-storey greenhouse in Lisse, The Netherlands under average day temperatures ranging from 12° to 22° C. and night temperatures ranging from 3° and 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season.*—June to October in The Netherlands.

*Plant habit.*—Herbaceous perennial, dwarf, globular in overall shape, broad and upright and spreading growth habit.

*Height and spread.*—About 21.4 cm in height and 35.8 cm in width.

*Hardiness.*—U.S.D.A. Zones 3 to 9.

*Diseases resistance.*—No susceptibility or resistance to diseases has been observed.

*Root description.*—Fibrous.

Growth and propagation:

*Propagation.*—Stem cuttings and tissue culture.

*Time from cutting to flowering.*—Average of 20 weeks.

*Crop maintenance.*—No pinching or pruning required.

*Growth rate.*—Low to moderate, 5 cm per month.

Stem description:

*Stem shape.*—Rounded.

*Stem aspect.*—Average 45° from horizontal, ranging from 25° to 90°.

*Stem strength.*—Moderate.

*Stem color.*—138C to 138D.

*Stem surface.*—Densely strigullose with strigose hairs averaging 1 mm in length, NN155D in color.

*Lateral branch length.*—Average of 15.7 cm.

*Lateral branch diameter.*—Average of 3 mm.

*Quantity of lateral branches.*—About 30 per plant.

*Internode length.*—Average of 1.7 cm.

*Branching.*—Freely branched.

Foliage description:

*Leaf division.*—Simple.

*Leaf shape.*—Oblanceolate to oblong.

*Leaf base.*—Short attenuate.

*Leaf apex.*—Broadly acute.

*Leaf margin.*—Entire to coarsely serrated.

*Leaf venation.*—Pinnate, 144D in color on upper and lower surface.

*Leaf attachment.*—Sessile.

*Leaf arrangement.*—Alternate.

*Leaf surface.*—Upper and lower surfaces; dull and moderately strigullose with strigose hairs about 0.8 mm in length and NN155D in color.

*Leaf color.*—Young foliage; upper surface 138A, lower surface 138B, mature foliage; upper surface 138A to 138B, lower surface 138B.

*Leaf size.*—Average of 10.2 cm in length and 3.2 cm in width.

Flower description:

General description:

*Inflorescence type.*—Terminal capitulum with many disc florets, one row of ray florets, and three rows of involucral bracts.

*Rate of flowering.*—Terminal inflorescence opens before lateral inflorescence.

*Lastingness of inflorescence.*—About 2 weeks, persistent.

*Fragrance.*—Moderately strong, slightly sweet.

*Quantity of inflorescences.*—1 per lateral stem, about 60 per plant.

*Inflorescence buds.*—About 9 mm in depth and 2.3 mm in diameter, flattened globular, color 153C to 153D with center 144B to 144C.

*Inflorescence size.*—About 3.2 cm in depth and 6.3 cm in diameter, diameter of disk about 2.5 cm.

*Receptacle.*—Flattened globular in shape, about 3 mm in depth, 5 mm in diameter, 157D in color.

*Peduncle.*—Round in shape, moderately strong, 145B in color with apex 145C to 145D, about 4.7 cm in length and 2 mm in diameter, slightly pubescent, hairs 0.8 mm in length and NN155D in color.

*Involucral bracts* (*phyllaries*).—28 per inflorescence, arranged in 3 rows, lanceolate to ovate in shape, acute apex, broadly cuneate base, margin entire and covered in villous hairs 1.5 mm in length NN155D in color, upper and lower surfaces dull and smooth, 138A in color becoming 138C to 138D towards base, about 1.3 cm in length and 4 mm in width.

Ray florets (capitulate):

*Number.*—Average of 17.

*Arrangement.*—Rotate, 1 whorl.

*Appearance.*—Smooth, dull, sparsely puberulent at base with hairs 0.8 mm in length, 157D in color.

*Shape.*—Obovate.

*Aspect.*—Outward to slightly downward at an angle of −5° from horizontal.

*Size.*—Average of 2.8 cm in length and 1.7 cm in width.

*Petal apex.*—Three-lobed.

*Petal base.*—Cuneate.

*Petal margins.*—Entire.

*Petal texture.*—Smooth, slightly ribbed lengthwise.

*Petal color.*—Opening; Upper surface a blend of N34A and 185A, apex 15A, lower surface a blend of 178B and 181A, apex 15A to 15B, fully open; upper surface 30B to 30C, apex 17C, lower surface 30C to 30D, apex 17C, senescing; upper surface 23B, apex 17B, lower surface 22A, apex 17C.

Disk florets (perfect):

*Quantity.*—Average of 100.

*Shape.*—Tubular.

*Arrangement.*—Spiral concentric towards center of disc.

*Petal apex.*—Free, narrowly acute, entire margin.

*Petal base.*—Fused.

*Petal texture.*—Upper surface; smooth, slightly glossy, lower surface; strongly hirsute, slightly glossy.

*Size.*—About 1.2 cm in length and 4 mm in width.

*Color.*—When opening; upper and lower surfaces 20B with mid-section and base 145C to 145D, mature; upper and lower surfaces 26A to 26B with mid-section and base 145C to 145D.

Reproductive organs:

*Presence.*—Disk flowers are perfect, ray flowers are carpellate.

*Gynoecium.*—1 pistil per disk and ray floret, 9 mm in length, stigma decurrent and 145C to 145D in color, style 6 mm in length and 157C to 157D in color, ovary 145D in color.

*Androecium.*—5 stamen per disk floret, filament 3 mm in length and 157D in color, anther linear in shape, about 3 mm in length and 13A in color, pollen moderate in quantity and 14A in color.

*Fruit and seed.*—No fruits or seeds observed to date.

It is claimed:

1. A new and distinct variety of *Gaillardia* plant designated 'Jazzy Wheeler' as described and illustrated herein.

* * * * *